(12) United States Patent
Le Thiesse

(10) Patent No.: US 7,235,299 B2
(45) Date of Patent: Jun. 26, 2007

(54) BEADS OF A PHENOLIC COMPOUND AND A METHOD OF OBTAINING SAME

(75) Inventor: Jean-Claude Le Thiesse, Saint-Etienne (FR)

(73) Assignee: Rhodia Chimie, Aubervilliers (FR)

( * ) Notice: Subject to any disclaimer, the term of this patent is extended or adjusted under 35 U.S.C. 154(b) by 0 days.

(21) Appl. No.: 10/532,743

(22) PCT Filed: Oct. 28, 2003

(86) PCT No.: PCT/FR03/03206

§ 371 (c)(1),
(2), (4) Date: Apr. 26, 2005

(87) PCT Pub. No.: WO2004/039758

PCT Pub. Date: May 13, 2004

(65) Prior Publication Data

US 2006/0135730 A1 Jun. 22, 2006

(30) Foreign Application Priority Data

Oct. 28, 2002 (FR) .................................. 02 13453

(51) Int. Cl.
*B32B 5/66* (2006.01)
(52) U.S. Cl. ........................ 428/402; 428/403; 428/407
(58) Field of Classification Search ................ 428/402, 428/403, 404, 407, 405, 406
See application file for complete search history.

(56) References Cited

U.S. PATENT DOCUMENTS 4,081,485 A * 3/1978 Eguchi ........................ 568/753

* cited by examiner

*Primary Examiner*—Leszek Kiliman

(57) ABSTRACT

The present invention relates to a novel presentation of a phenolic compound in the solid form. More particularly, the invention provides beads of hydroquinone. The invention also pertains to the preparation of said beads. The process of the invention is characterized in that a hot concentrated aqueous solution of a phenolic compound is prepared, then the solution is fragmented into droplets and the droplets obtained are cooled in a gas stream so that they solidify into beads which are then recovered and dried.

41 Claims, No Drawings

BEADS OF A PHENOLIC COMPOUND AND A METHOD OF OBTAINING SAME

This application is an application under 35 U.S.C. Section 371 of International Application Number PCT/FR03/03206 filed on Oct. 28, 2003.

The present invention relates to a novel presentation of a phenolic compound in the solid form. More particularly, the invention provides hydroquinone beads. The invention also pertains to the preparation of said beads.

Hydroquinone is a product that is widely used in many fields as a polymerization inhibitor or as an antioxidant in elastomers. A further field of application is in photography. Thus, it is a product that is used in large quantities.

Hydroquinone is currently available on the market in the form of a powder crystallized in the form of needles. As a result, it suffers from the presence of fines which cause problems with fluffing during storage and manipulation of said powder.

Hydroquinone powder is not without danger to the environment because of the risks of explosion and because this substance is an irritant for the eyes and the respiratory tract and can also cause skin irritation on contact.

Japanese patent JP-A-2002-302 716 describes a technique for granulating hydroquinone, which consists of passing the powder between two rollers to produce tablets, then crushing the tablets to obtain granules.

The disadvantage of that process is that dust can subsist in the in the granulated product either because of the passage through the rollers, breaking the crystals in the rollers of the compacter, or by attrition of the tablets in the crusher. Further, the granules are compact and their rate of dissolution is very low compared with the initial powder.

The present invention aims to provide a novel presentation of a phenolic compound, in particular hydroquinone, to overcome said disadvantages.

More precisely, the present invention provides beads of a phenolic compound, more particularly beads of hydroquinone.

Said beads have the characteristics of attrition resistant while being porous which give them solubility properties.

The term "beads" will be used in the present invention to define solid, highly spherical particles.

The invention also pertains to a process for preparing said beads, characterized by preparing a hot concentrated aqueous solution of a phenolic compound then fragmenting the solution into droplets and cooling the droplets obtained in a stream of gas so that they solidify into beads which are then recovered and dried.

The term "concentrated solution" means a solution with a concentration that approaches saturation, preferably 80% to 95% by weight of the solubility limit, at the temperature of the fractionation device.

A preferred variation of the process of the invention consists of preparing a hot concentrated solution of a phenolic compound then passing the solution through a nozzle to form droplets, solidifying the latter by allowing them to fall in a tower with a counter-current of a cold gas then recovering the anal beads obtained and drying them.

The process of the invention is perfectly adapted for the preparation of hydroquinone beads, but it is also suitable for any phenolic compound with the following characteristics:
- a high hot solubility, for example a solubility in water of at least 500 g/l for a reference temperature of 90° C., preferably at least 1000 g/l; the upper limit is not critical but it is generally less than 15000 g/l/
- a large difference between hot and cold solubilities, i.e. between the temperature in the fragmentation device and the temperature of the cooling gas stream: these solubilities preferably differ by a factor of at least two and more preferably at least three to five.

Examples of phenolic compounds to which the process of the invention can be applied that can be mentioned are those with the following formula (I):

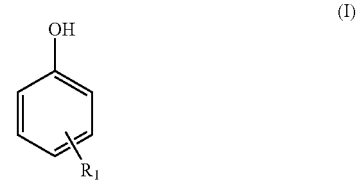

in which formula (I), $R_1$ represents a hydroxyl group, an amino group, an alkyl group containing 1 to 4 carbon atoms or an alkoxy group containing 1 to 4 carbon atoms.

This list of substituents $R_1$ is given by way of illustration and is in no way limiting provided that the compound employed has the physico-chemical characteristics defined above.

Specific examples of compounds with formula (I) that can in particular be cited are hydroquinone, pyrocatechine, resorcin and m-aminophenol.

Preferably, the invention is applicable to hydroquinone.

The process of the invention has characteristics which are peculiar to it and which can thus produce the phenolic compound in the form of beads.

The beads obtained of the invention have the physico-chemical characteristics defined above.

The definitions and the methods for determining the characteristics given above are described in the examples.

The beads of phenolic compound are in the form of white beads. Because of the process of the invention, said particles, which are essentially spherical in shape, have a diameter that can fall within a wide range. The particle size can be from 100 µm to 3000 µm, but is preferably in the range 500 µm to 1500 µm. Note that the size is determined by passage through metal sieves.

Generally, the particle size, expressed by the median diameter ($d_{50}$), is in the range 300 µm to 2000 µm, preferably in the range 500 µm to 1500 µm. The median diameter is defined as being such that 50% by weight of the particles have a diameter that is greater than or less than the median diameter.

FIG. 1 shows an optical microscope photograph showing the bead type morphology of the hydroquinone obtained in accordance with the invention. Note the uniform granulometric distribution in the product obtained.

The hydroquinone beads have a density which can vary. The apparent density (loose) of the beads is preferably at least 0.3 and more preferably is in the range 0.4 to 0.5. it should be noted that the density of the beads of the invention is lower than that of the crystallized powder. However, they are far less compressible as their degree of compressibility, which is between 5% and 10%, is 3 to 4 times lower than that of the crystallized powder.

In accordance with the process of the invention, beads of a phenolic compound of the invention are obtained which are free of dust and which have a physical form which endows them with good attrition resistance during transport and storage operations.

Attrition resistance is determined by a test carried out using an air jet sieve (type Alpine 200 LS-N) provided with a sieve with a mesh of 100 μm. Attrition resistance is expressed as the ratio between the weight of the beads remaining on the sieve and the initial weight of the beads.

The beads obtained have an attrition resistance of between 90% and 100%, preferably more than 95% and more preferably more than 98%.

Thus, the invention resides in beads of a phenolic compound, preferably hydroquinone which, while having a physical form that endows them with attrition resistance, has a substantial internal porosity and thus a rapid dissolution rate during use.

It should be noted that the beads have an internal porosity, determined in a mercury porosimeter, in the range 0.5 to 0.75 $cm^3/g$.

By way of illustration, the rate of dissolution at 20° C. for a concentration of 5% by weight of hydroquinone in methyl methacrylate is almost halved in the case of beads when compared with a powder. Whether the hydroquinone is in the form of powder or in the form of the beads of the invention, its rate of dissolution in an amount of 2% in acrylic acid is identical.

The original structure of the products of the invention is obtained by dint of a perfectly adapted production process.

The process of the invention for preparing beads of a phenolic compound consists of preparing a hot concentrated aqueous solution of a phenolic compound then fragmenting the solution into droplets and cooling the droplets obtained in a stream of gas so that they solidify into beads which are then recovered and dried.

The process of the invention is suitable for preparing hydroquinone beads. Said process uses the prilling technique but in contrast to normal practice, it does not consist of melting the hydroquinone and then fragmenting it by passage through a nozzle.

The difficulty encountered by the skilled person is that hydroquinone melts at a high temperature of 172° C.; further, hydroquinone has a very high vapour tension (more than 25 mbars at this temperature) which means that at the nozzle outlet, substantial vaporization causes problems with dust and cleaning, which are a redhibitory problem from an industrial viewpoint.

The Applicant has discovered that it is possible to prepare beads of a phenolic compound using the prilling technique starting from an aqueous solution of a phenolic compound.

In accordance with the process of the invention, we obtain beads of a phenolic compound by exploiting the fact that the solubility of said compound, in particular hydroquinone, decreases drastically as the temperature is dropped.

More precisely, in the defined temperature zone, the phenolic compound is soluble then re-crystallizes as soon as the temperature of its aqueous solution falls.

It is important in the first step to prepare an aqueous solution of a phenolic compound in a concentration that is as close as possible to saturation at the temperature under consideration.

The temperature of the solution is selected so as to be sufficiently high to obtain a solubility of at least 500 g/l, preferably 1000 g/l.

It is advantageously selected so as to be between 80° C. and 98° C., preferably between 85° C. and 95° C.

In this temperature range, it can be specified by way of indication that the solubility of hydroquinone in water is in the range 0.9 to 1.7 kg per kg of water.

In the next step, the solution of the phenolic compound is transformed into droplets. This operation can be carried out using any fragmentation device, for example a turbine, a spray nozzle, or a flat nozzle with circular orifice(s).

In a preferred implementation, the droplets are formed by passing the solution through an orifice and in particular passage through a nozzle.

The next operation ensures that the droplets solidify into beads by contact with a cold gas the temperature of which is between −30° C. and 30° C., preferably between −10° C. and 10° C.

The cold gas can be any gas, provided that it is inert towards the phenolic compound, preferably hydroquinone. Preferably, nitrogen or oxygen-depleted air (depleted to 10%, for example) is selected.

Preferably, the cold gas stream is sent as a counter-current to the stream of material.

The residence time, namely the period between formation of the droplet at the nozzle outlet and its arrival in the recovery system, is advantageously between 1 and 10 seconds, more preferably between 3 and 5 seconds.

One way of obtaining the desired residence time is to allow the droplets to fall in a tower as a counter-current to a cold gas, as cited above.

At the end of the reaction, beads are recovered using any known means, for example under gravity in a recovery vessel or using the fluidized bed technique.

The beads obtained are in the form of a solid that can be manipulated, but they also include water.

Generally, the beads of phenolic compound comprise:
10% to 50% by weight of water;
50% to 90% by weight of a phenolic compound.

In the case of hydroquinone, the beads preferably comprise:
25% to 50% by weight of water;
50% to 75% by weight of hydroquinone.

In accordance with the process of the invention, a subsequent step can be carried out for drying the beads obtained following the prilling operation.

To this end, the beads are subjected to a stream of gas, preferably a stream of air the temperature of which is in the range 20° C. (ambient temperature) to 90° C., preferably in the range 60° C. to 90° C.

Drying is advantageously carried out using the fluidized bed technique; the temperature is progressively raised in said temperature zone.

At the end of the operation, beads are obtained with a water content that is generally less than 1% by weight, in the range 0.1% to 1%, preferably less than 0.6%.

The apparatus used to carry out the process of the invention it composed of two assemblies; a first assembly for forming the beads and a second assembly for recovering and drying the beads.

The first assembly comprises a storage tank for the phenolic compound provided with means for heating the solution of the phenolic compound, in particular a jacket in which a liquid, for example water, circulates at the desired temperature, and a chamber which is generally a tower comprising a device for fragmentation into droplets in its upper portion, preferably a nozzle, and provided in its lower portion with one or more inlets for a cold gas stream, transforming the bottom of the tower into a cooling tower.

The height of the tower can vary widely, for example between 3 and 40 meters depending on the size of the facility. It should be noted that the upper limit is not critical.

The phenolic compound and water are introduced into a reactor provided with a system for regulating the temperature, for example a jacket, to maintain said compound in aqueous solution.

The nozzle used can be a single- or multi-holed nozzle with a number of holes which can be from 1 to 3000 holes, preferably between 1 and 100 holes.

It is possible to use a system comprising a plurality of nozzles, for example 2 nozzles, preferably removable, in parallel.

The diameter of the nozzle perforations is a function of the desired bead size. It may be 50 to 2000 µm, but is preferably between 200 µm and 600 µm.

The perforation size is always smaller than the size of the bead obtained. A nozzle with perforations of about 300 µm can be used to obtain beads with a median diameter of 500 µm.

The nozzle used can be a static nozzle, but it is possible to use a nozzle that is vibrated electrically at a high frequency, for example 100 to 10000 hertz. That device can produce droplets with a perfectly calibrated size.

The solution arrives in the nozzle, preferably at an overpressure ensured by a stream of gas, preferably a stream of nitrogen. The overpressure with respect to the atmospheric pressure is 5% to 500%.

The nozzle is maintained at a temperature of more than 2° C. to 10° C. with respect to the temperature at which crystallization of the aqueous solution of the phenolic solution commences.

It is possible but not vital to establish a stream of gas, preferably a stream of nitrogen which is a co-current with the jet leaving the nozzle. Said gas stream is preferably at a temperature in the range from ambient temperature to 80° C. The presence of said gas co-current improves the dimensional regularity of the beads and prevents the beads from coalescing.

In the upper portion of the tower, chicanes and grilles may be present on the inner wall of the tower, to allow a homogeneous distribution of the gas stream.

A stream of cold gas, preferably nitrogen or oxygen-depleted air, is introduced into the bottom of the tower. Said cold gas stream ensures that the droplets solidify into beads. Preferably, it is at a temperature in the range −30° C. to 30° C., preferably in the range −10° C. to 10° C.

The cold gas stream preferably leaves the tower below the nozzle at a distance representing about one tenth of the total height of the cooling zone.

The nature of the bead recovery system at the bottom of the tower is not critical. It may be a recovery tank or a device that can fluidize the bed of particles. It is constituted by a tank, preferably cylindrical, comprising a grille in its lower portion through which a gas stream, preferably nitrogen or oxygen-depleted air, is sent. The gas flow rate, which depends on the particle size, must be such that it maintains the particles in suspension. By way of example, we can specify that it is 5 to 30 m³/h for a fluidized bed diameter of 80 mm.

The fluidization device has an outlet for evacuating beads to any drying device suitable for carrying out this operation, in particular a fluidized bed or an oven.

One embodiment of the invention is illustrated in the accompanying drawing, FIG. 2.

FIG. 2 is a diagrammatic side view of an apparatus that is suitable for carrying out the invention.

The apparatus used is constituted by two portions: the upper portion or prilling tower (A) and the lower portion, which shows a fluidization device (B).

The solution of the phenolic compound is introduced into a jacketed storage reactor tank (1) and then is guided towards a nozzle (2). For this purpose, nitrogen (3) is admitted into the tank (1) at an overpressure.

The tower is 8 meters high, comprising a nozzle (2) in its upper portion that can optionally be integral with a vibrator (4), and is provided with an inlet for a diameter of cold oxygen-depleted air (5) in its lower portion.

The cooling air introduced at (5) leaves the tower at point (6) below the nozzle (2).

In the upper portion of the tower are chicanes (7) and a ring-shaped grille (8) for homogeneous distribution of the gas stream in the tower. In a variation, which is not shown in this embodiment, it is possible to send a stream of hot nitrogen (9) with a temperature in the range 20° C. to 80° C., preferably in the range 60° C. to 80° C., distributed as a co-current around the nozzle (2).

In the lower portion of the tower, a truncated conical grille (10) collects the solidified beads in a fluidizing bed device comprising an inlet for cold air (11) and an outlet (12) for continuously evacuating the beads obtained to a fluidized bed type drying device, not shown in the figure.

An example of the invention will now be given by way of non-limiting illustration.

Before describing the examples, we shall describe the methods used to determine the different characteristics of the products obtained.

The Median Diameter:

This is determined by passing the powder through a sieve.

The Compact and Loose Apparent Density:

This is measured using the apparatus illustrated in FIG. 3.

Firstly, an empty measuring cylinder (2) is weighed.

The powder to be measured is introduced into the measuring cylinder (2) using a funnel (1) so that the top of the bed of powder comes up to the top of the measuring cylinder, calibrated at 250 cm³ (level A).

The mass of powder is determined by weighing the full measuring cylinder.

The measuring cylinder is fixed to a support (3) via grips (4).

The counter (8), which totalizes the number of shocks made on the bottom of the measuring cylinder, is zeroed.

The measuring cylinder is then subjected to vertical shocks applied to its base via a hammer (5) activated by a motor (6) via a cam (7). The operation is stopped when the volume obtained is constant (level B).

The change in the apparent volume read on the graduations of the measuring cylinder is recorded as a function of the number of shocks applied using the hammer.

An experimental compaction curve is obtained.

Apparent volume=$f$(number of shocks), which is transformed into a curve of apparent density=$f$ (number of shocks).

The apparent density is determined before and after compaction using the relationship:

$$\text{Apparent density} = \frac{\text{mass of powder introduced }(g)}{\text{Apparent volume }(cm^3)}$$

The compressibility is determined according to the relationship:

$$\text{Compressibility} = \frac{\text{compact density} - \text{loose density}}{\text{Compact density}}$$

Attrition Resistance:

The attrition resistance is determined by means of a test carried out with an air jet sieve (type Alpine 200LS-N) provided with a sieve with a mesh of 100 μm.

This mesh is selected as it is generally admitted by the skilled person that particles with a diameter of less than 100 μm are susceptible of generating dust during manipulation of a powder.

Under the action of a stream of air traversing the sieve, the beads are regularly projected against the cover of the sieve and subjected to friction on the metallic structure of the sieve.

Those movements perfectly simulate the shocks and mechanical stresses to which beads can be subjected during transport and storage.

The test consists of placing 40 g of beads on the 100 μm sieve then causing the sieve to operate at an underpressure of 3200 Pa for 5 minutes.

By weighing the quantity of beads remaining on the sieve at the end of the test, we can deduce the quantity of particles with a size of less than 100 μm which have been generated during the test.

The attrition resistance is expressed as the ratio between the mass of beads remaining on the sieve and the initial mass of beads.

Internal Porosity:

The internal porosity of the beads is measured using a mercury porosimeter in accordance with the ASTM Standards on Catalysts D 4284-92.

EXAMPLE

1) This example illustrates the preparation of hydroquinone beads. They were prepared in an apparatus as shown in FIG. 2.

The nozzle, which was not vibrated, had a 0.5 mm diameter hole and an L/D ratio of 3; L represents the length of the orifice and D represents the orifice diameter.

We started from 1500 g of a crystallized hydroquinone powder and 1228 g of water, preferably demineralized.

The hydroquinone powder and water were introduced into the reactor (1).

The hydroquinone was dissolved in the reactor (1) by heating using hot water circulating in the water jacket. The temperature of the product was 94° C. at (1) and the temperature at (2) at the nozzle outlet was 92.5° C.

The nitrogen overpressure at (3) was close to 0.1 bars.

The flow rate of the aqueous solution at the nozzle outlet at (2) was 1.8 kg/h.

Cooling air was introduced at (5) at a temperature of 0° C. and a flow rate of 850 m³/h, giving a speed in the tower of 0.6 m/s.

The temperature of the air leaving at (6) was 3.5° C.

The beads obtained were collected at (10).

The compositions of the beads at the bottom of the tower was 68% by weight of hydroquinone and 32% by weight of water.

The beads collected at (10) were recovered in a fluidized bed (11). The temperature of the fluidizing air at (11) was 20° C.

The beads were evacuated at (12) for drying in a fluidized bed with air at a temperature in the range 60° C. to 90° C.

The composition of beads obtained after drying was 99.64% by weight of hydroquinone and 0.36% by weight of water.

The beads obtained had the following characteristics:
a median diameter ($d_{50}$) of 1350 μm;
a loose apparent density of 0.436;
a compact apparent density of 0.462;
an attrition resistance of 99.5%;
a compressibility ratio of 5.6% (compared with that of crystalline hydroquinone, namely 20.4%);
an internal porosity of 0.54 cm³/g;
a dissolution time of:
  10 minutes in acrylic acid at 20° C. (idem for crystalline hydroquinone);
  and 1 min 45 sec in methyl methacrylate at 20° C. (3 min for crystalline hydroquinone).

What is claimed is:

1. Beads of a phenolic compound having a high hot solubility of at least 500 g/l at a reference temperature of 90° C., and a difference of solubility which is at least doubled between its hot solubility in a first operational temperature in a fragmentation apparatus and cold solubility in a second operational temperature in a cooling gas stream, said beads being both attrition resistant and porous.

2. The beads according to claim 1, wherein the phenolic compound has a high hot solubility of at least 1000 g/l at a reference temperature of 90° C.

3. The beads according to claim 2, wherein the difference of solubility is a multiple of at least 3 to 5 times between said two operational temperatures.

4. The beads according to claim 1, wherein the phenolic compound has the following formula (I):

wherein:
  $R_1$ represents a hydroxyl group, an amino group, an alkyl group having 1 to 4 carbon atoms or an alkoxy group having 1 to 4 carbon atoms.

5. The beads according to claim 4, wherein the phenolic compound is selected from hydroquinone, pyrocatechin, resorcin or m-aminophenol.

6. The beads according to claim 1, having a particle size of between 100 μm and 3000 μm.

7. The beads according to claim 1, having a size, expressed as the median diameter ($d_{50}$), of from 300 μm to 2000 μm.

8. The beads according to claim 1, having an attrition resistance of between 90% and 100.

9. The beads according to claim 1, having an internal porosity, determined using a mercury porosimeter, of between 0.5 and 0.75, and having a bulk density (loose) of at least 0.3.

10. The beads according to claim 5, having a degree of compressibility of 5% to 10%.

11. The beads according to claim 5, having an attrition resistance of more than 98%.

12. The beads according to claim 5, wherein having an internal porosity, determined using a mercury porosimeter, of between 0.5 and 0.75 cm³/g.

13. A process for preparing the beads defined in claim 1, comprising the steps of:
a) preparing a hot concentrated aqueous solution of a phenolic compound, then,
b) fragmenting the solution into droplets and cooling the droplets obtained in a stream of gas so that they solidify into beads, and, then,
c) the beads obtained in step b) are recovered and dried.

14. The process according to claim 13, wherein step b) consists of passing the phenolic acid solution through a nozzle to form droplets, solidifying the latter by allowing them to fall in a tower with a counter-current of a cold gas, in order to obtain the beads.

15. The process according to claim 14, wherein step a) consists of preparing the aqueous solution of a phenolic compound at a concentration of at least 500 g/l.

16. The process according to claim 15, wherein the aqueous solution of step a) is at a temperature of between 80° C. and 98° C.

17. The process according to claim 14, wherein in step b), the nozzle is a single-hole nozzle or a multi-hole nozzle having between 1 and 3000 holes.

18. The process according to claim 14, wherein in step b), the nozzle has perforations whose diameter is between 50 and 2000 µm.

19. The process according to claim 17, wherein the nozzle is a static nozzle, preferably a nozzle which is subjected to a high frequency electrical vibration system, at 100 to 10000 hertz.

20. The process according to claim 13, wherein in step b), the gas is nitrogen or oxygen-depleted air whose temperature is between −30° C. and 30° C.

21. The process according to claim 14, wherein the droplet has a residence time for the nozzle outlet to its arrival of between 1 and 10 seconds.

22. The process according to claim 13, wherein in step c), the beads are being recovered using a fluidized bed technique.

23. The process according to claim 13, wherein in step b) the beads are formed in a prilling tower and the beads of phenolic compound at the bottom of the prilling tower is:
10% to 50% by weight of water; and
50% to 90% by weight of phenolic compound.

24. The process according to claim 23, wherein the phenolic compound is hydroquinone and the composition at the bottom of the prilling tower is:
25% to 50% by weight of water;
50% to 75% by weight of phenolic compound.

25. The process according to claim 13, wherein in step c), the beads are subjected to a stream of air the temperature of which is in the range 20° C. to 90° C., optionally in the range 60° C. to 90° C.

26. The process according to claim 25, wherein drying is carried out using a fluidized bed technique.

27. The process according to claim 26, wherein the beads of phenolic compound after drying is as follows:
0.1% to 1% by weight of water; and
99% to 99.9% by weight of phenolic compound.

28. The process according to claim 27, in which the composition of the beads of phenolic compound after drying is as follows:
0.1% to 0.6% by weight of water;
99.4% to 99.9% by weight of phenolic compound.

29. The beads according to claim 1, wherein the phenolic compound has a high hot solubility of less than 15000 g/l.

30. The beads according to claim 6, having a particle size of between 500 µm and 1500 µm.

31. The beads according to claim 7, having a size, expressed as the median diameter ($d_{50}$), of from 500 µm to 1500 µm.

32. The beads according to claim 8, having an attrition resistance of more than 98%.

33. The beads according to claim 9, having a bulk density (loose) of between 0.4 and 0.5.

34. The beads according to claim 11, having an attrition resistance of between 90% and 100%.

35. The process according to claim 15, wherein step a) consists of preparing the aqueous solution of a phenolic compound at a concentration of at least 1000 g/l.

36. The process according to claim 16, wherein the aqueous solution of step a) is at a temperature of between 85° C. and 95° C.

37. The process according to claim 17, wherein in step b), the nozzle is a single-hole nozzle or a multi-hole nozzle having between 1 and 100 holes.

38. The process according to claim 18, wherein in step b), the nozzle has perforations whose diameter is between 200 and 600 µm.

39. The process according to claim 20, wherein in step b), the gas is nitrogen or oxygen-depleted air whose temperature is between −10° C. and 10° C.

40. The process according to claim 21, wherein the droplet has a residence time for the nozzle outlet to its arrival of between 3 and 5 seconds.

41. The beads according to claim 29, wherein the phenolic compound is hydroquinone.

* * * * *